(12) United States Patent
Berra et al.

(10) Patent No.: US 8,292,949 B2
(45) Date of Patent: Oct. 23, 2012

(54) METHODS AND APPARATUS FOR TREATMENT OF THORACIC AORTIC ANEURYSMS

(75) Inventors: Humberto Berra, Cooper City, FL (US); Trevor Greenan, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 771 days.

(21) Appl. No.: 11/750,678

(22) Filed: May 18, 2007

(65) Prior Publication Data
US 2007/0233229 A1      Oct. 4, 2007

Related U.S. Application Data

(63) Continuation-in-part of application No. PCT/US2006/034340, filed on Sep. 1, 2006.

(60) Provisional application No. 60/713,595, filed on Sep. 1, 2005.

(51) Int. Cl.
*A61F 2/06* (2006.01)

(52) U.S. Cl. ........... 623/1.35; 623/1.13; 623/1.15
(58) Field of Classification Search ........... 623/1.1, 623/1.13, 1.15, 1.35, 1.14
See application file for complete search history.

(56) References Cited

U.S. PATENT DOCUMENTS

| | | | |
|---|---|---|---|
| 6,524,335 B1 | 2/2003 | Hartley et al. | |
| 6,648,913 B1 | 11/2003 | Yee et al. | |
| 6,663,667 B2 | 12/2003 | Dehdashtian et al. | |
| 6,773,457 B2 | 8/2004 | Ivancev et al. | |
| 2005/0102018 A1* | 5/2005 | Carpenter et al. | 623/1.11 |
| 2005/0149168 A1* | 7/2005 | Gregorich | 623/1.15 |
| 2005/0222669 A1* | 10/2005 | Purdy | 623/1.13 |

* cited by examiner

*Primary Examiner* — Christopher D Koharski
*Assistant Examiner* — Matthew Schall

(57) ABSTRACT

Methods and apparatus for aiding in support and repair of a thoracic aneurysm of the aortic arch. A stent graft provides a window therein, which enables blood to flow freely into branch vessels which would otherwise be occluded by the stent graft. Additionally, the stent portions of the stent graft are configured to minimize the risk of overexpansion, wherein stents are provided in the window portion.

1 Claim, 12 Drawing Sheets

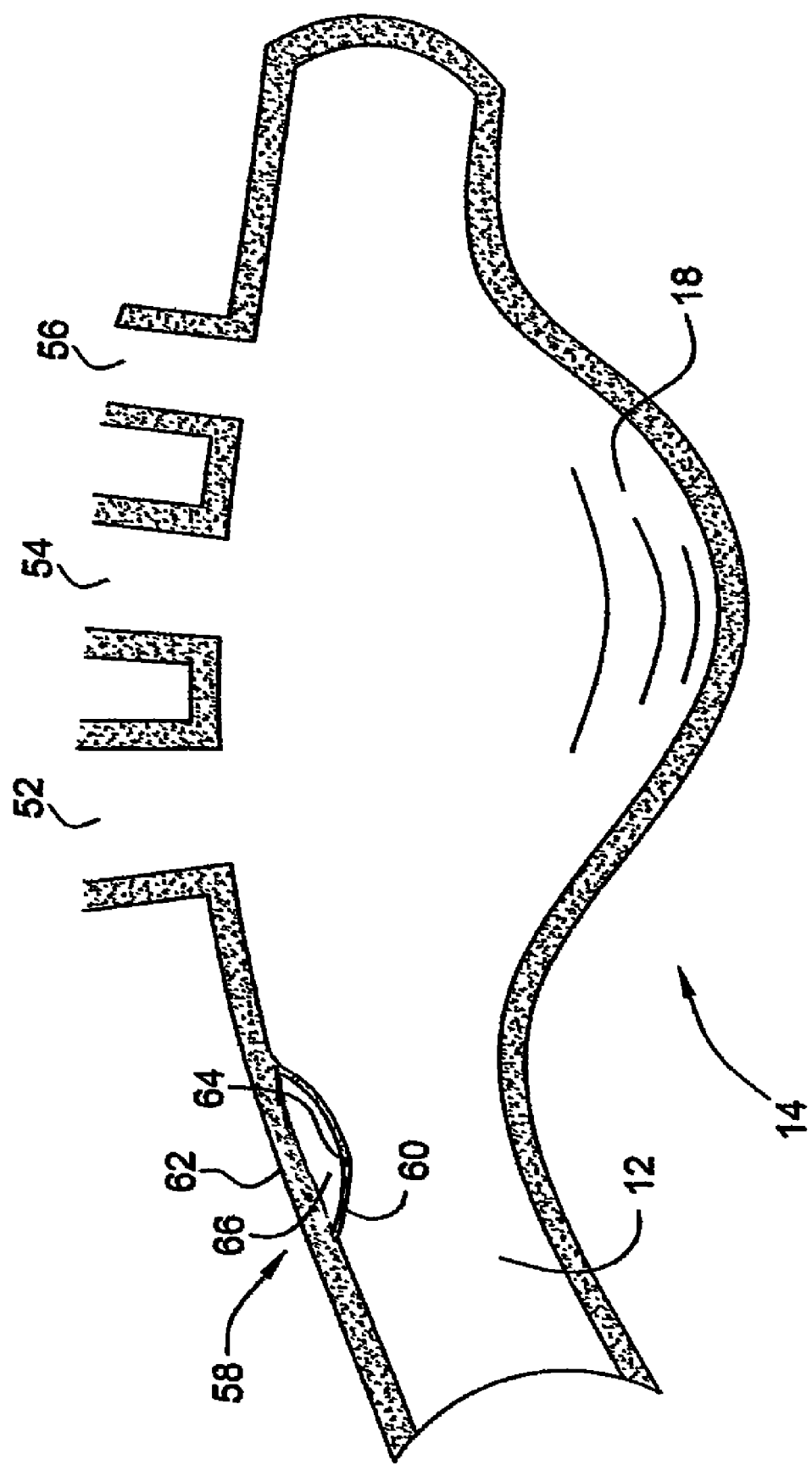

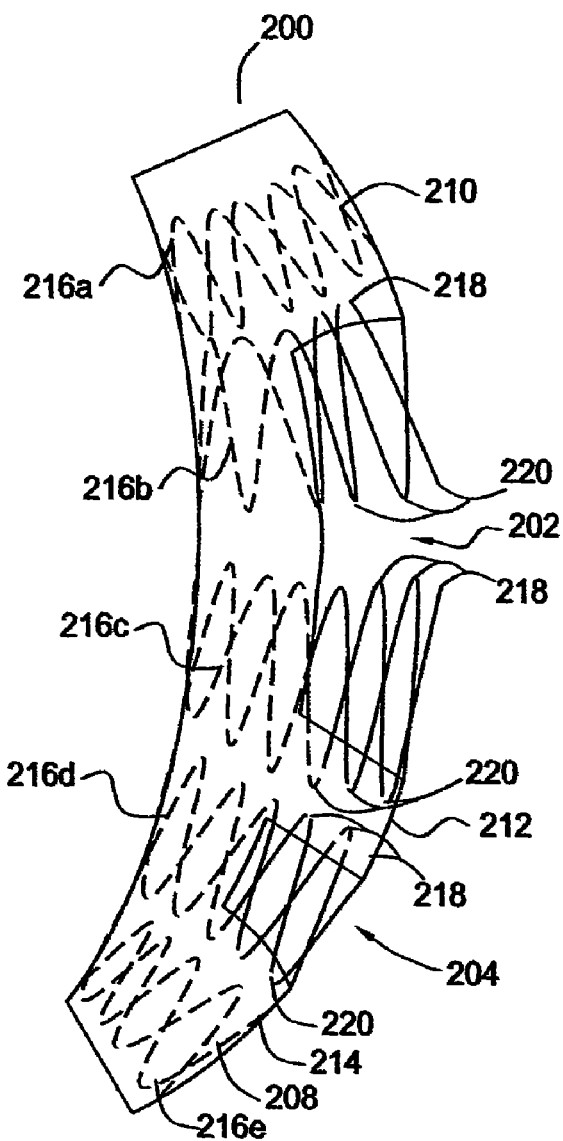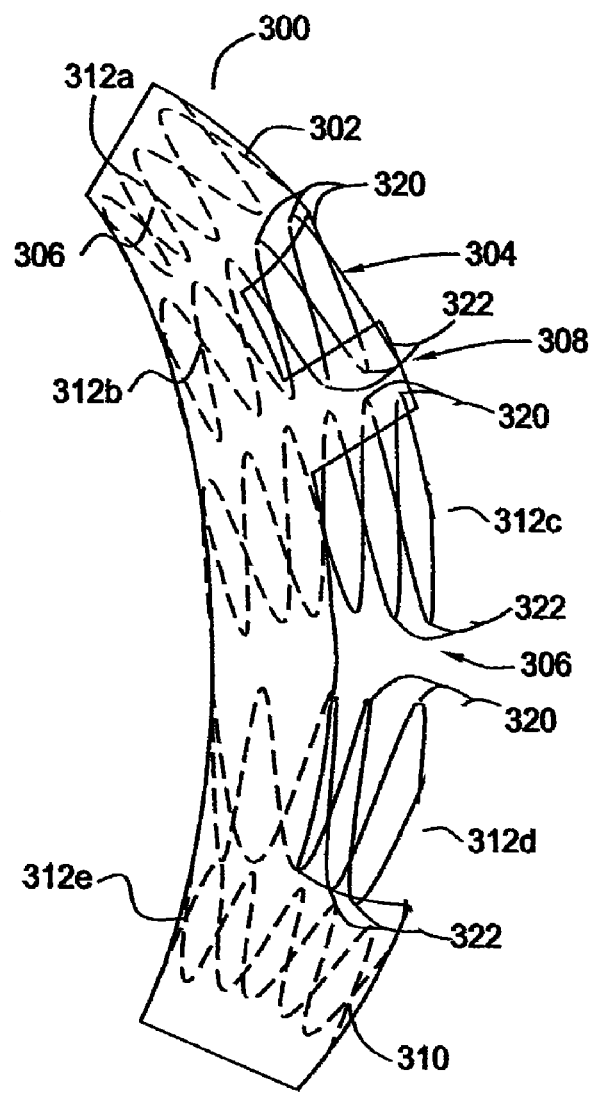
FIG. 4C
FIG. 4D

METHODS AND APPARATUS FOR TREATMENT OF THORACIC AORTIC ANEURYSMS

RELATED APPLICATIONS

This application is a continuation-in-part of PCT/US2006/034340 filed on Sep. 1, 2006; which claims priority to U.S. Provisional Patent Application 60/713,595 filed Sep. 1, 2005, all of which are incorporated herein by reference.

FIELD OF THE INVENTION

The field of the invention is the treatment of vascular abnormalities and defects.

BACKGROUND OF THE INVENTION

"Thoracic aortic aneurysm" is the term used to describe a condition where a segment of the aorta in the thoracic region is dilated and is treatable when it reaches more than 50% of its original diameter. Thoracic aortic aneurysms are known to be caused by hardening of the arteries (atherosclerosis), high blood pressure (hypertension), congenital disorders such as Marfan's Syndrome, trauma, or less commonly, syphilis. Atherosclerosis is by far the most common cause. Thoracic aneurysms occur in the ascending aorta (approximately 25% of the time), the aortic arch (approximately 25% of the time) or the descending thoracic aorta (approximately 50% of the time).

The thoracic aorta has numerous arterial branches. The arch of the aorta has three major branches extending therefrom, all of which arise from the convex upper surface of the arch and ascend through the superior thoracic aperture to the root of the neck. The brachiocephalic artery originates anterior to the trachea. The brachiocephalic artery divides into two branches, the right subclavian artery (which supplies blood to the right arm) and the right common carotid artery (which supplies blood to the right side of the head and neck). The left common carotid artery arises from the arch of the aorta just to the left of the origin of the brachiocephalic artery. The left common carotid artery supplies blood to the left side of the head and neck. The third branch arising from the aortic arch, the left subclavian artery, originates behind and just to the left of the origin of the left common carotid artery and supplies blood to the left arm.

When an aneurysm of the aorta occurs, most patients have no symptoms until the aneurysm begins to leak or expand. Most non-leaking thoracic aneurysms of the aortic arch are detected by tests—usually a chest x-ray or a chest CT scan—that are run for other reasons. Chest or back pain may indicate acute expansion or leakage of the aneurysm. An aortogram (a special set of x-ray images made as a result of injection of dye into the aorta) also may identify the location and extent of the aneurysm and identify any branch arteries of the aorta that are also involved. For patients with thoracic aneurysms of the aortic arch, surgery to replace the aorta may be performed where the aorta is replaced with a fabric substitute in an operation that uses a heart-lung machine. In such a case, the aneurysmal portion of the aorta is removed or opened and a substitute lumen is sewn across the aneurysmal portion. Such surgery is highly invasive, requires an extended recovery period and, therefore, cannot be performed on individuals in fragile health or with other contraindicative factors.

Alternatively, the aneurysmal region of the aorta can be bypassed by use of a tubular exclusion device, e.g., by a stent graft placed inside the vessel spanning the aneurysmal portion of the vessel, to seal off the aneurysmal portion from further exposure to blood flowing through the aorta. A stent graft can be implanted without a chest incision, using specialized catheters that are introduced through arteries, usually through incisions in the groin region of the patient. The use of stent grafts to internally bypass, within the aorta or flow lumen, the aneurysmal site, is also not without issues. In particular, where a stent graft is used in a thoracic location, care must be taken so that critical branch arteries are not covered or occluded by the stent graft yet the stent graft must seal against the aorta wall and provide a flow conduit for blood to flow past the aneurysmal site. Where the aneurysm is located immediately adjacent to the branch arteries, there is a need to deploy the stent graft in a location which partially or fully extends across the location of the origin of the branch arteries from the aorta to ensure sealing of the stent graft to the artery wall. However, there is not presently an acceptable paradigm for enabling flow to the branch artery when a stent graft is deployed.

Additionally, where an aneurysm develops, an aortic dissection may develop as a side effect of the thinning of the aorta wall during an aneurysmal event or as a consequence of the weakening of the aorta wall which brought on the aneurysmal event. When such dissection occurs, an inner lumen wall layer and an outer lumen wall layer of the aorta become separated, such that a gap may form therebetween. If blood can access this gap, such as through a tear in the inner wall of the aorta, the dissection may increase in size and the inner blood vessel wall layer may extend inwardly of the flow lumen, reducing the flow cross-section for blood flow therethrough and forming a region between the inner and outer lumen wall layers where blood can collect under systemic pressure. This blood may further aggravate the aneurysmal condition, increasing the risk of a rupture of the aneurysm. Such a dissection may occur adjacent to, and extend from, the aneurysmal aortic site, such that the placement of a stent graft to exclude the aneurysm may not address the dissected lumen condition and fresh blood can access the dissection and perhaps, through the region between the lumen walls, supply fresh blood to the aneurysm leading to further progression thereof.

Thus, there is a desire in the art to achieve a greater success of aneurysm repair and healing of the aortic arch, and to address the dissected lumen wall condition.

SUMMARY OF THE INVENTION

Embodiments according to the present invention address aneurysm repair and stabilization. Specifically, a stent graft for use in the treatment of thoracic aneurysms of the aortic arch that spans the aneurysmal region, while not blocking or otherwise impeding the flow of blood to the three arteries that branch off of the aortic arch.

Thus, in one embodiment according to the invention there is provided an intravascular treatment device, comprising various embodiments of a window configured stent graft locatable at an aneurysmal site in the aortic arch. The treatment device may, additionally, provide localized radially outward pressure over a dissected area of the lumen, which can extend from the aneurysmal location and may extend adjacent to the branch artery locations.

BRIEF DESCRIPTION OF THE DRAWINGS

A more particular description of the invention, briefly summarized above, may be had by reference to the embodiments according to the invention described in the present specification and illustrated in the appended drawings.

FIG. 3 is an artist's rendering, in cutaway, of the aneurysmal aortic arch of FIG. 1, including a dissected portion thereof;

FIGS. 4A, 4B, 4C and 4D are side views of various embodiments of the stent graft according to the present invention.

DETAILED DESCRIPTION

Methods and apparatus for stabilizing and treating an aneurysm of the aortic arch include positioning an endovascular stent graft with various branch artery aligned window configurations in an aneurysmal site in the aortic arch. The stent graft excludes blood flow to the weakened vessel wall at the aneurysmal site, but, as a result of the window configuration, allows unimpeded blood flow from the aortic arch to the brachiocephalic trunk, the left common carotid artery, and the left subclavian artery.

Figure 1:
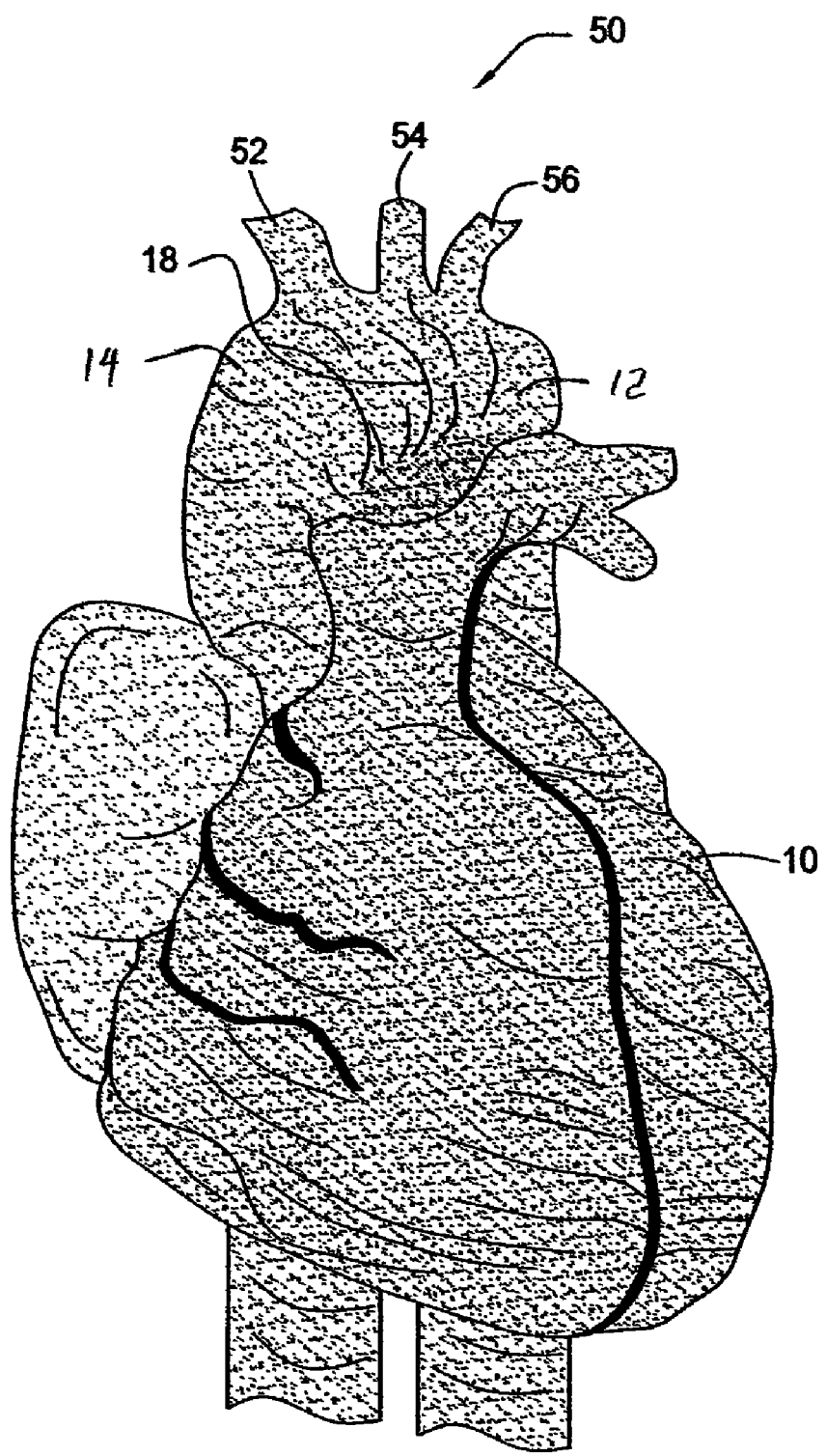
FIG. 1 is an artist's rendering of a heart and aorta with a thoracic aneurysm of the aortal arch.
Figure 2:
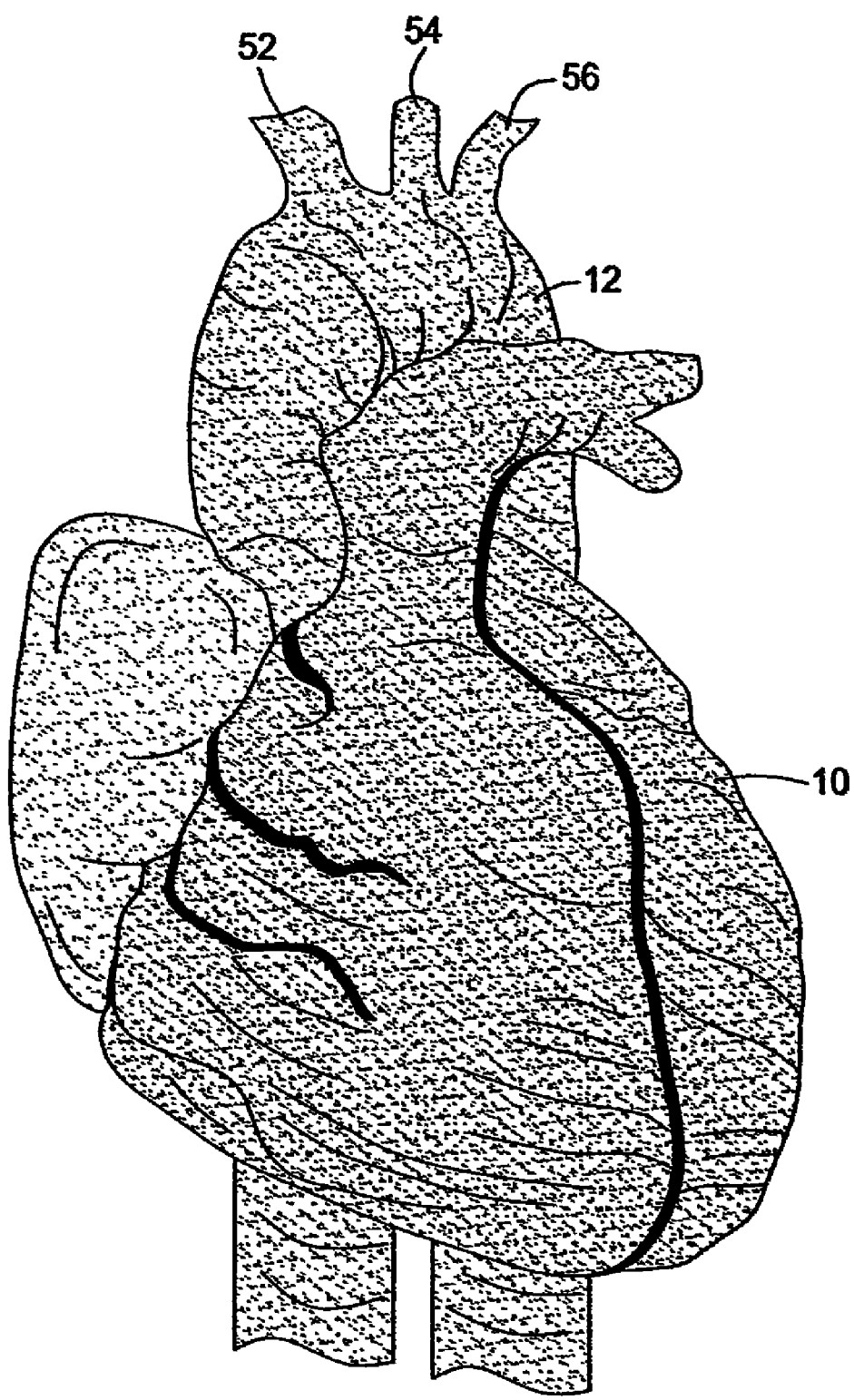
FIG. 2 is an artist's rendering of an the heart and aortic arch of FIG. 1, wherein the aortic arch is in a healthy condition.

Referring initially to FIG. 1, there is shown an aneurysm of the aorta 12, such that the aorta is enlarged at an aneurysmal site 14. The aneurysm at the aneurysmal site 14 forms an aneurysmal bulge or sac 18 which is a weakened portion of the aorta wall which is less capable of supporting the systemic blood flow pressure than adjacent regions. As a result of this loss of strength, as well as loss of elasticity, the aorta wall expands outwardly into a bulge or sac 18. If left untreated, the aneurysmal sac 18 may continue to deteriorate, weaken, increase in size, and eventually tear or burst. The heart 10, the aortic arch 50, with three branching arteries, the brachiocephalic trunk (52), the left common carotid artery (54), and the left subclavian artery (56) are shown, such that they are diametrically opposed to, or circumferentially adjacent to, the aneurysmal sac 18. Typically, an aneurysmal aortic condition is considered to require treatment if the diameter of the aorta, including the aneurysmal sac 18, exceeds 150% of the diameter of the healthy aorta. The aorta 12 wall extends circumferentially outwardly at the aneurysmal site 14 to form the aneurysmal sac 18, at which aorta 12 wall location the aorta wall 12 is stretched and weakened, in comparison to the aorta 12 of FIG. 2, where no aneurysm is present and the aorta 12 wall remains non-distended such that the diameter of the aorta 12 is relatively uniform as it extends away from the heart in the direction of, and past, the branch arteries, 52, 54, and 56.

Referring now to FIG. 3, an artist's rendition of the aorta 12 of FIG. 1 is shown with the aneurysmal region of the arch in a cutaway view, such that the effect of the aneurysm upon the aorta wall is clear. In this Figure, the aneurysmal sac 18 is present, in the aorta 12, intermediate of the heart (not shown, but to the left, in FIG. 3) and adjacent to the branch arteries 52, 54, and 56. Also present, in this aorta 12, is a dissected region 58, where the blood vessel inner wall (layer) 60 has pulled away from the blood vessel outer wall (layer) 62, in a position in the aorta adjacent to (upstream from) the location of the branch arteries 52, 54, and 56. Also present is a tear 64, in the inner aorta wall (layer) 60, through which blood, under systemic pressure, can reach the gap 66 formed between the inner and outer layers of the aorta wall 60 and 62. Thus, for treatment of these aortic conditions, a single stent graft will need to span and form a synthetic flow lumen past the aneurysmal sac 18, seal off blood supply through the tear 64 and may be configured to compress (or press) the aorta inner wall layer 60 with the outer wall layer 62 forming the dissection.

Figures 4A, 4B:
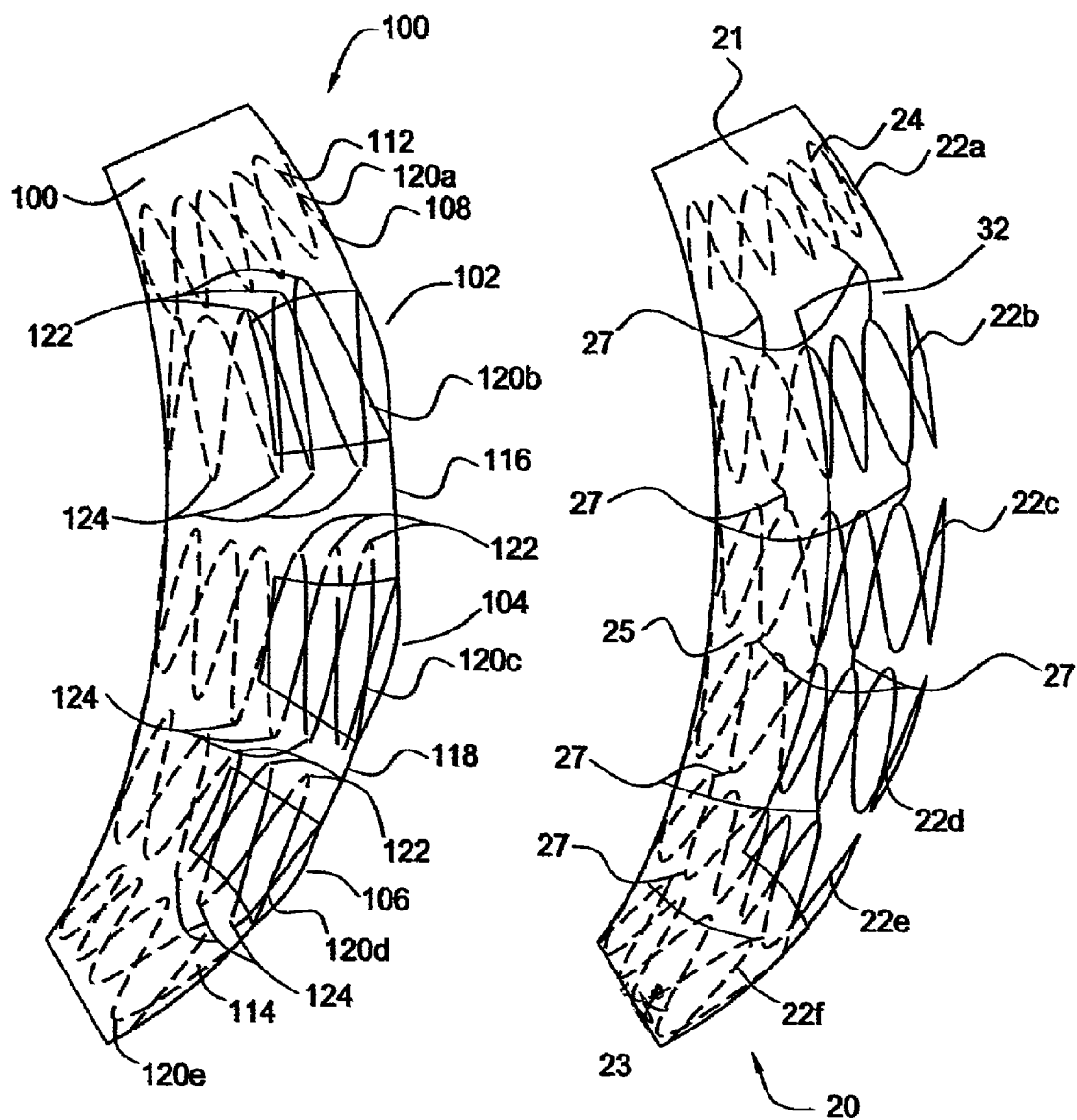

FIGS. 4A, 4B, 4C, and 4D are side views of embodiments of a stent graft according to the present invention, which are capable of providing the sealing off of the aneurysmal sac 18 and the tear 64, while pressing the aorta inner wall layer 60 toward the outer wall layer 62 adjacent to the tear 64. In each embodiment of the stent graft shown in these Figures, there is provided a synthetic flow lumen to bypass or exclude the aneurysmal sac 18 and likewise seal off and compress (or press or exert force on) the dissected aorta wall 12 adjacent to the branch arteries 52, 54, and 56 while simultaneously allowing blood flow to the branch arteries 52, 54, and 56. Generally, the stent grafts of the embodiments can be considered to include one with a single window configured to span the location of all three of the branch arteries (FIG. 4B), a configuration with a discrete window for each branch artery (FIG. 4A), and configurations where one window accommodates a single one of the branch arteries and a second window accommodates the remaining two of the branch arteries (FIGS. 4C and 4D).

Figure 5:
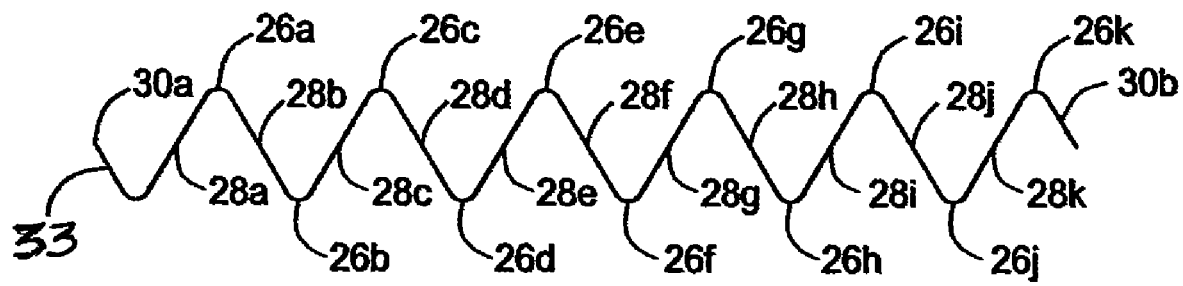
FIG. 5 is a plan view of a preform of the stent portion of the stent graft.
Figure 6:
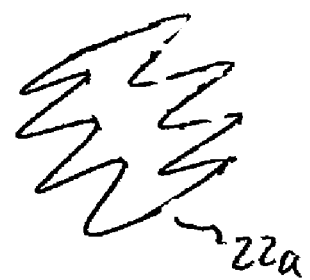
FIG. 6 is a perspective view of the preform of FIG. 5, further configured as a stent.

Referring initially to FIG. 4B, there is shown generally a stent graft 20 comprising a series of stents 22a, 22b ... 22f. in a cylindrically formed framework, having a graft portion 24, having a single window 32 therein, disposed over the stents 22a, 22b, etc. To form the stent graft 20, a plurality of stents 22a, 22b, etc. must be formed, and secured to a tubular graft portion 24 structure which will be described in further detail. To form the stents 22a through 22f, a wire 33 (FIG. 5), in the embodiments shown in FIGS. 4 (4A to 4D), made of Nitinol, is formed into a zig-zag pattern such as shown in FIG. 5. In this configuration, this forms a plurality of staggered, opposed apexes 26a, 26b, et. seq. separated by substantially straight sections (struts) 28a, 28b, et. seq. terminating in opposed ends 30a, 30b. Once formed as shown in FIG. 5, the zig-zag wire is formed into a hoop, as shown in FIG. 6 (where a plurality of hoop shaped stents are shown), such that ends 30a and 30b are joined, to create each of stents 22a, et. seq.

Figure 7:
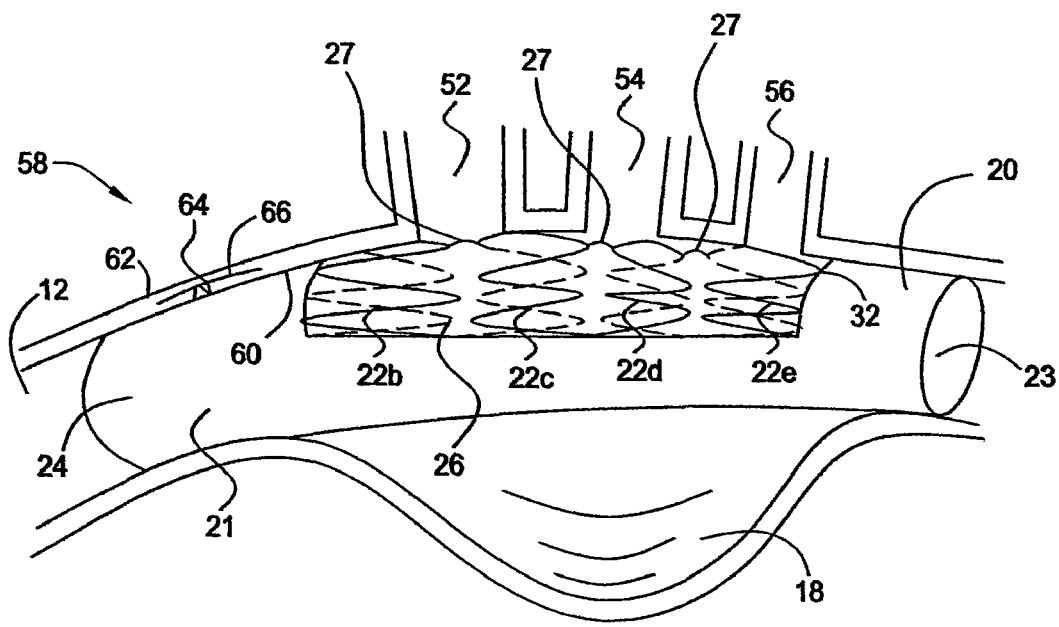
FIG. 7 is a partial sectional view of a thoracic aneurysm of the aortal arch of FIG. 3 with the embodiment of the stent graft shown in FIG. 4B located therein.

To form the graft portion 24 of the stent graft 20 of FIG. 4B, a length of tubular woven bio-compatible polyester of the length and diameter desired for exclusion of the aneurysmal sac 18 and also of sufficient length to span the branch arteries shown as 52, 54, and 56 in FIG. 3, is selected, and the fabric is cut (or otherwise configured) to form a window 32 therethrough as shown in FIG. 4B. The length and width of the window are selected to ensure that the window 32, when the stent graft 20 is deployed in the aneurysmal; aorta 12, spans opening of the branch arteries 52, 54, and 56 from the aorta 12, yet, the portion of the graft material 24 circumferentially adjacent to the window can push against, and seal against, the aorta wall, to exclude blood flow to the aneurysmal sac 18 as shown in FIG. 7. To seal the cut edges of the window 32, the fabric adjacent thereto is subject to a temperature sufficient to cause the material to reform slightly (or be cauterized or melt). The tubular woven fabric forming the graft may be of a single piece of material, or of multiple pieces of material sewn or otherwise attached together. Once the window 32 is cut or formed in the graft material, the remaining graft material forms first and second hoops 21, 23, and a spanning semicircumferential portion 25 extending therebetween across the underside, or opposed to, the window 32. The stents 22a through 22f are then compressed and placed inside of the graft portion 24, and allowed to expand against the inner surface of the material forming the graft portion 24. Each of the stents 22a-22f is individually sewn to the adjacent graft material, to secure the stents 22a-22f to the graft portion 24. As shown in FIG. 4B, the stents 22a and 22f are located within, and fully supported against, an enveloping portion of the graft portion 24 formed by first and second hoops 21, 23, and stents 22b, 22c, 22d and 22e are located such that a portion thereof extend about the perimeter of the window 32, in a position substantially mimicking the position of the graft material removed to form the window 34 as if the graft material were not removed to form the window 34. Stents 22b-22e are maintained in the stent graft by being sewn, or otherwise affixed to, the semi circumferential portion 25. Additionally, spanning wires (connecting bars) 27, of the same material and diameter of the wire comprising the stents 22a, et. seq., may be deployed between adjacent stents, typically between adjacent apexes thereof, in three or four locations about the circumference of the stents 22a-22f, such as shown between stents 22a and 22b, and crimped or otherwise affixed thereto, to maintain additional rigidity of the stent graft between the stents 22a, et. seq. Further expansion limiting hoop wires or strong durable fibers (not shown) can be employed to assure that the stents positioned in the open area 32 of the graft do not expand substantially beyond the limits of the tubular configuration of the thoracic side opening stent graft whose diameter along its length is approximated by the graft portion 24 surrounding the first and second hoops 21, 23. The expansion limiting hoop wires can be sewn or crimped to the individual stents in the opening or can be part of flexible lattice work that allows the tubular structure to bend as needed to confirm to the aortic arch, but minimizes the chance that a potion of a stent will end up in an undesired position or configuration outside the confines of a curved cylinder that tracks to and through the aortic arch mimicking the aorta itself.

The stent graft 20 of FIG. 4B is shown, deployed, in FIG. 7, wherein the window 34 is aligned with the branch arteries 52, 54, and 56 such that no portion of the graft portion 24 of the stent graft 20 overlays the intersection of the aorta 12 with any one of branch arteries 52, 54, or 56. The opposed hoops 21, 23 of the stent graft 20 are engaged against the inner aorta wall 60 and seal the stent graft aorta wall interface, and the portion of the graft spanning partial-circumferential portion 25 adjacent to the opening of the window 32 through the graft material 24 likewise is expanded against, and seals against, the aorta inner wall 60 to seal off the passage of blood from the interior of the stent graft 20 to the aneurysmal sac 18. Additionally, the portion of the stent graft 20 overlying the dissected region 58 of the aorta presses the inner wall layer 60 toward the outer wall layer 62 of the aorta 12 (together) and likewise seals the tear 64 in the aorta inner wall 60. Thus, blood flow through the aorta 12 is excluded from the aneurysmal sac 18, the dissection region 58 is closed off from fresh blood supply through the tear 64, and the inner and outer walls of the aorta 12, otherwise separated at the dissection region 58, are pushed together.

One problematic issue inherent in the in the use of the stent graft 20 shown in FIG. 4B is the contact between the partially unsupported portions of stents 22b, 22c, 22d, and 22e, i.e., stents deployed such that the outward extension thereof is not limited by a full hoop of graft material, and the aorta 12 wall. These partially unsupported stents 22b-22e must provide sufficient circumferential force, when deployed, to seal the portions of the semi-circumferential spanning portion 25 adjacent to the window 32 against the adjacent aorta inner wall 60, yet they must not overload or overextend (overexpand) into the aorta wall 60 in such a manner as to cause damage thereto. In the embodiment shown in FIG. 4B, the stents 22b-22e which are positioned within the window 32 are partially unrestrained, as they are not surrounded and thus not completely bounded and compressed by the graft portion 24 as are stents 22a and 22f. Thus, the stents 22b-22e may overextend into and damage the aorta 12 wall. In particular, there is a risk, in the event of overextension of the stents 22b-22e, that an apex such as apex 26a may puncture or tear the aorta 12 wall. To prevent this occurrence, (if the hoop wire/lattice work configuration discussed earlier is not used) the relaxed circumference of the partially unrestrained by the graft portion stents 22b-22e may be smaller than that of the restrained stents 22a-22f. Preferably, the restrained stents 22a, 22f have a relaxed (or unrestrained) circumference larger than that of the inner circumference of the graft portion 24 in the region of the graft portion 24 in which they are to be located, i.e., the first and second hoops 21, 23 and the partially unrestrained stents 22b to 22e have a circumference which is the same size, or slightly smaller, on the order of, or slightly smaller than, the inner circumference of the graft portion 24 in its unbiased by the stent portions 22a or 22f state or condition. Thus, the maximum extension of the stent portions 22b-22e is on the order of the free or unbiased circumference of the graft portion 24, and thus overextension of the stents 22b to 22e is prevented, yet sufficient force is exerted radially by the stent portions 22b to 22e against the aorta 12 wall to cause the semi-circumferential spanning portion 25 of the stent graft 20 to seal against the aorta wall at locations where it contacts the aorta 12 wall adjacent to the window 32.

Referring now to FIG. 4A, there is shown a further embodiment according to the present invention, in which the single window 32 of the embodiment shown in FIG. 4B is replaced with a stent graft 100 having a plurality of individual windows 102, 104, and 106, each one configured to span the opening of each branch artery 52, 54, and 58 from the aorta 12. To form these windows, graft material 110 having a length sufficient to span an aneurysmal sac 18 and enable sealing of the stent graft 100 with aortic wall tissue at either side thereof is further processed by cutting three generally rectangular or circular segments out of its tubular wall 108. The windows 102, 104, and 106 are each located in the graft material 110 to correspond, when stent graft 100 is deployed, with a location of one of the branch artery 52, 54, 56 intersection locations with the aorta 12. Again, as with stent graft 20, the location of the cut in the graft material 110 is heat cauterized to prevent fraying. The cutting of the three windows 102, 104 and 106 provides, longitudinally adjacent to the windows, a series of continuous hoops of the graft material 110. These hoops include inlet hoop 112, outlet hoop 114, first intermediate hoop 116 and second intermediate hoop 118. Window 102 is located between inlet hoop 112 and first intermediate hoop 116, window 104 is located between first intermediate hoop 116 and second intermediate hoop 118, and window 106 is located between second intermediate hoop 118 and outlet hoop 114.

To prepare stent graft 100, stents 120, having the same configuration as the stents described herein with reference to FIGS. 5 and 6, are located within the graft material 100 having the windows 102, 104, and 106 previously formed therein. In the configuration of stent graft 100 shown, five stents, 120a to 120e, are used. Stents 120a and 120e are shown in phantom, and are fully received within, and restrained by, inlet hoop 112 and outlet hoop 114 respectively. Stent 120b spans the window 102, but its opposed apexes 122, 124 are received within, and restrained by, inlet hoop 112 and first intermediate hoop 116. Likewise stent 120c is disposed to span window 104, such that the opposed apexes 122, 124 are located within, and are restrained by, first intermediate hoop 116 and second intermediate hoop 118. Likewise, stent 120d spans window 106, and the opposed apexes 122, 124 thereof are disposed within, and restrained by, second intermediate hoop 118 and outlet hoop 114. As with the configuration of stent graft 20 of FIG. 4B, spanning wires (not shown) may be deployed between adjacent stents 120a, 120b, etc.

Figure 8:
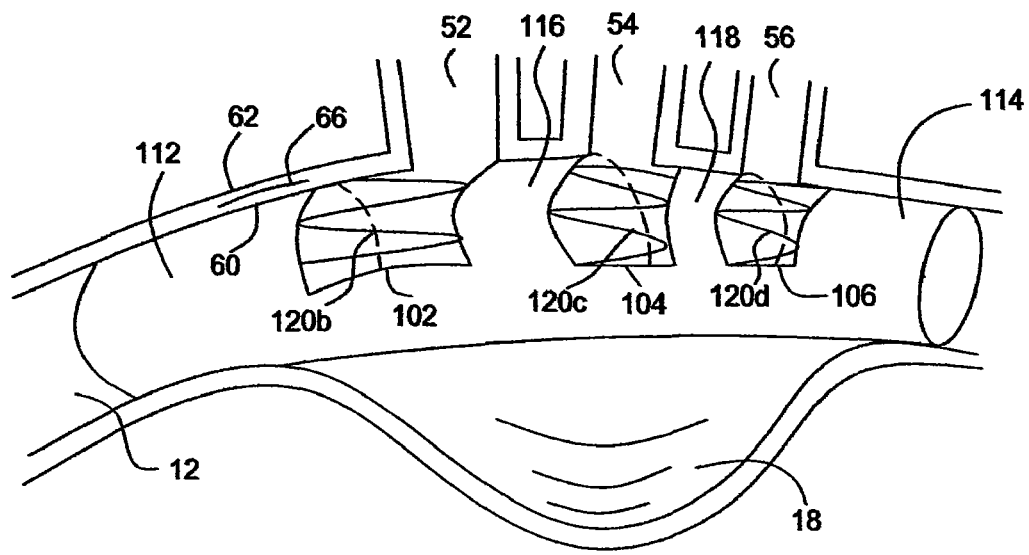
FIG. 8 is a partial sectional view of a thoracic aneurysm of the aortal arch with an embodiment of the stent graft shown in FIG. 4A placed therein.
Figure 10:
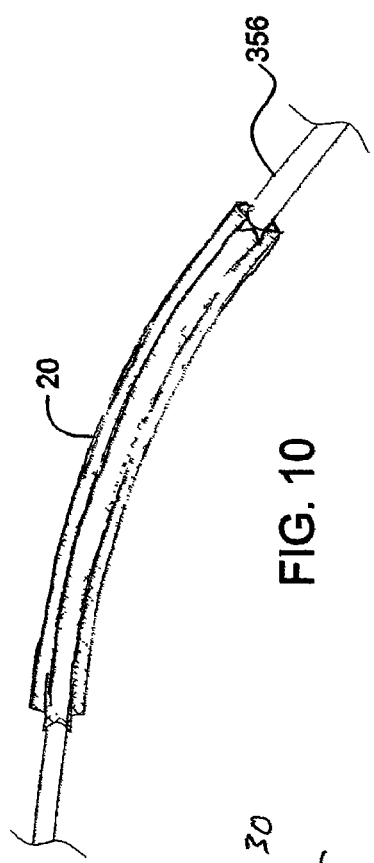
FIG. 10 is a perspective view of the stent graft in FIG. 9 compressed to a size smaller than the internal circumference of the sheath of a delivery catheter.

In contrast to the structure of stent graft 20, wherein their exists a need to differentially size the restrained stents 22a, 22f as compared to unrestrained stents 22b-22e, the retraining capability provided by the hoops 112-118, and the positioning of the apexes 122, 124 of the stents 120b-120d within these hoops 112-118, helps prevent overextension of the stents 120b-120d disposed across the windows 102, 104 and 106 and thus enables the use of stents of equal circumference throughout the stent graft 100. Additionally, the hoops 112-118 provide additional sealing and pressing capacity to seal against the aorta wall adjacent to and intermediate of the branch arteries 52, 54, and 56, as shown with the deployed stent 100 in an aneurysmal aorta as shown in FIG. 8. However, the use of three individual windows 102, 104, and 106 requires more precision, during deployment, to ensure that each window corresponds to a branch artery location.

Referring now to FIG. 4C, an additional embodiment of a stent graft 200 useful for the treatment of aneurysm of the aortic arch is shown. In this embodiment, the stent graft 200 includes two windows 202, 204, the first window 202 sized to span branch arteries 52 and 54 (the arteries as shown in FIG. 3), and a second smaller window 204 sized to span the position of the intersection of branch artery 56 and the aorta 12 (as such are shown in FIG. 3). As with the embodiments of FIGS. 4A and 4B, the stent graft 200 of this embodiment is constructed by cutting the windows 202, 204, in a tubular length of graft material 208 of sufficient length to span the aneurysmal sac 18 (as the sac is shown in FIG. 3) and sufficient diameter, when deployed, to seal against the aorta 12 wall. Window 202 is located between an inlet hoop 210 and an intermediate hoop 212. Window 204 is located between intermediate hoop 212 and an outlet hoop 214, each of the hoops 210, 212 and 214 formed of a continuous circumferential loop of graft material. In this embodiment, five stents 216a-e of the construction shown and described with respect to FIGS. 5 and 6 are used. Stent 216 is fully received within inlet hoop 210, and stent 216e is fully received within exit hoop 214. Two stents 216b and 216c are disposed in window 202, such that the apexes 218 of stent 216b are received within and restrained by inlet hoop 210 and apexes 220 thereof within the window 202 are unrestrained, and the apexes 220 of stent 216c are received in and restrained by intermediate hoop 212, but apexes 218 thereof are unrestrained in the window 202. Each of the stents 216a-216e is secured in the stent graft 200, preferably by sewing the stents 216a-e to adjacent portions of the graft material 210. Likewise, spanning wires, not shown, may be used to secure the stents 216a-e in a fixed longitudinal or spaced relationship, and provide additional hoop or radial strength to the stent graft 200 structure. Stent 216d spans second window 204, with the opposed apexes 218, 220 thereof received within, and restrained by, intermediate hoop 212 and exit hoop 214 respectively.

As with the stent graft 20 of FIG. 4B, the stents 216b and 216c are, at least partially, unrestrained. Therefore, if lattice work hoop expansion limiting structures (described above) are not used stents 216b and 216c are preferably sized to have a slightly smaller circumference than the remainder of stents 216a, 216d and 216e, on the order of the unbiased by a stent circumference of the graft material 208. When deployed in an aorta 12 having an aneurysmal condition, the window 202 will span the location of the intersection of the branch arteries 52 and 54, (FIG. 3), and window 204 will span the location of branch artery 56. Alternatively, the stents 216b and 216c may be fully unrestrained, i.e., the apexes thereof not inserted within the adjacent hoops, and of a smaller circumference than stents 216a, d, and e as was discussed with respect to the stent graft 20 of FIG. 4B. Likewise, an additional stent may be located in the envelope of, and fully restrained by, intermediate hoop 212.

Referring now to FIG. 4D, an additional embodiment of a stent graft for treatment of ascending aortic aneurysm is shown. In this embodiment, stent graft 300 includes a tubular length of graft material 302, into which two windows 304, 306 have been prepared such as by cutting out rectangular portions of the graft material 202 and heat sealing or cauterizing the cut edges to prevent fraying. Window 304 is sized to correspond with the location of the intersection of a single branch artery 52, and window 306 is sized to correspond to the location of two branch arteries, 54 and 56. The remaining graft material forms an inlet hoop 306, an intermediate hoop 308 and outlet hoop 310. Stents 312a-312e are disposed in the tubular segment of graft material 302, such as by being sewn to adjacent portions of the graft material 302. The stents 312a-312e have the general construction of the stents shown and described with respect to FIGS. 5 and 6, and stents 312a and 312e are fully located within, and restrained by inlet hoop 306 and outlet hoop 310 respectively. Stent 312 b spans window 304, such that the opposed apexes 316, 318 thereof are restrained within inlet hoop 306 and intermediate hoop 308, respectively. Stents 312c and 312d are disposed in window 306 such that the apexes 320 of stent 312c are restrained by intermediate hoop 308 and apexes 322 thereof are unrestrained in the window 306, and stent 312d is positioned such that apexes 322 are held and restrained under exit hoop 310, whereas the apexes 320 thereof are unrestrained. As in the construction shown in FIG. 4C, the two stents 312c, 312d which are unrestrained, are configured of a smaller circumference than those which are restrained, to prevent damage to the flow lumen by overextension of the stents 312c, 312d. Likewise, spanning wires may laterally extend between, and be secured to, adjacent ones of the stents 312a, et. seq. When deployed in an aorta undergoing an aneurysmal condition, the inlet hoop and outlet hoops 302, 310 will seal against the aorta wall, and the graft material 302 is likewise biased to seal against any tears which it overlays and compress together any dissected regions it overlays. As with stent graft 200, stents 312c, d may be unrestrained, and of a slightly smaller diameter than stents 312a, b and e, as was described wherein with respect to FIG. 4B. Likewise, an additional stent may be located within, and fully restrained by, intermediate hoop 308.

Figure 9:
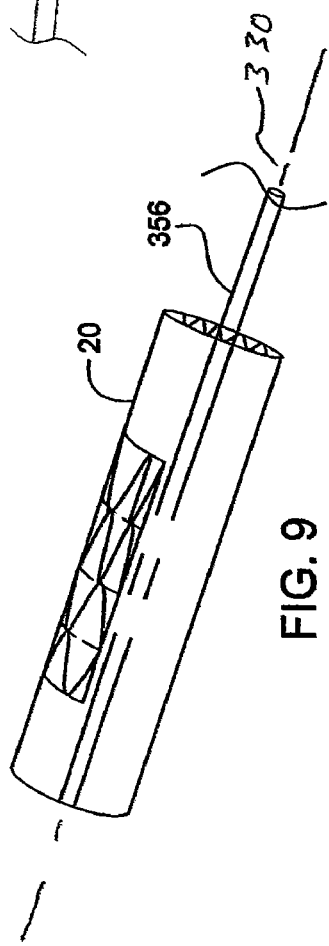
FIG. 9 is a perspective view of the stent graft of FIG. 4B, positioning around a delivery catheter in preparation for being compressed and having a delivery catheter moved into position surrounding it.
Figure 11:
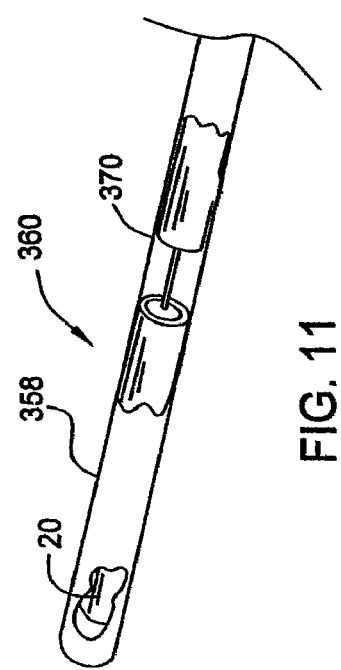
FIG. 11 is a partial view of a schematic view of the sheath of the delivery catheter, partially cut-away, showing the stent graft received therein.
Figure 12:
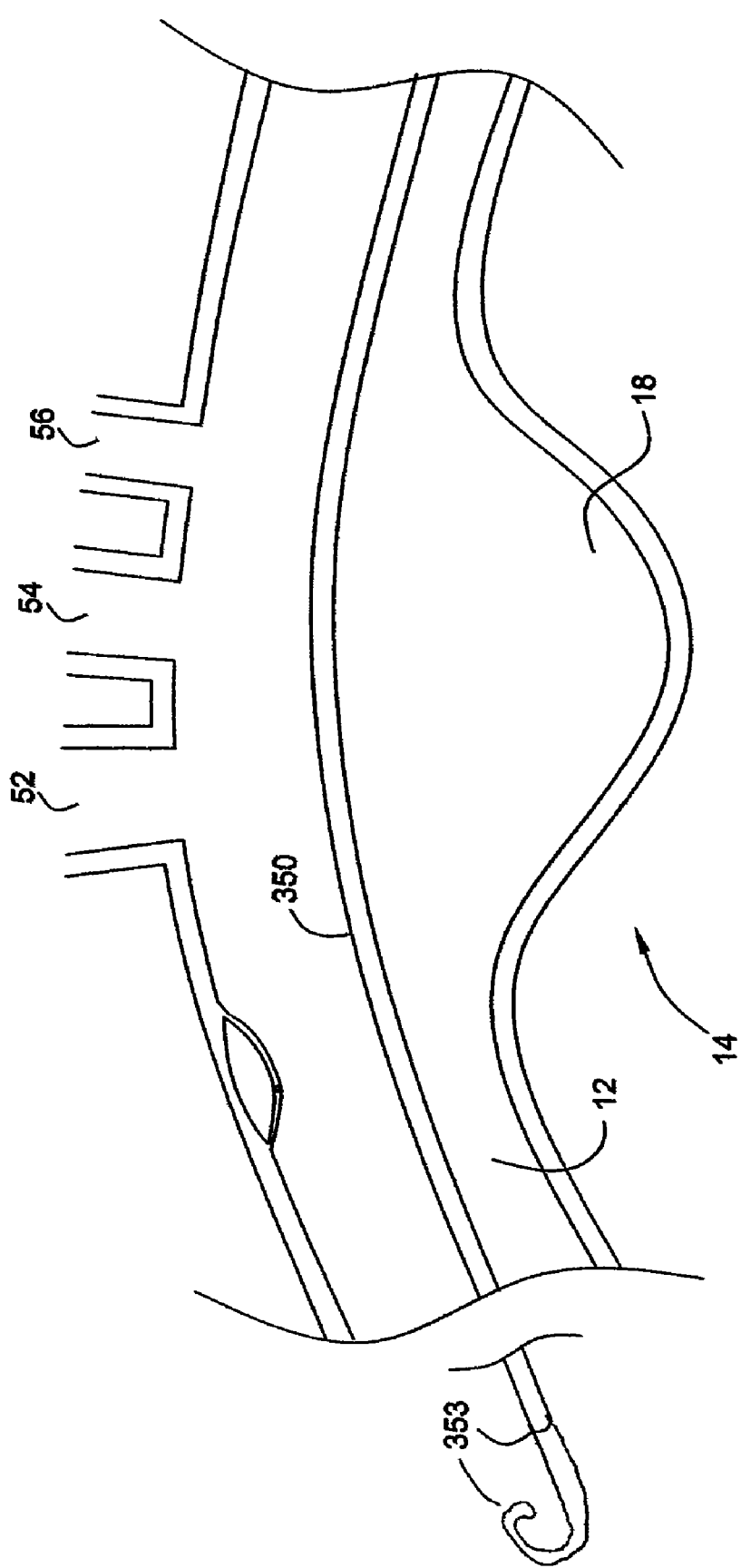
FIG. 12 is a partial cutaway view of an aortic arch undergoing aneurysm, having the guide wire needed to guide a catheter to the aneurysmal location shown extending therethrough.
Figure 13:
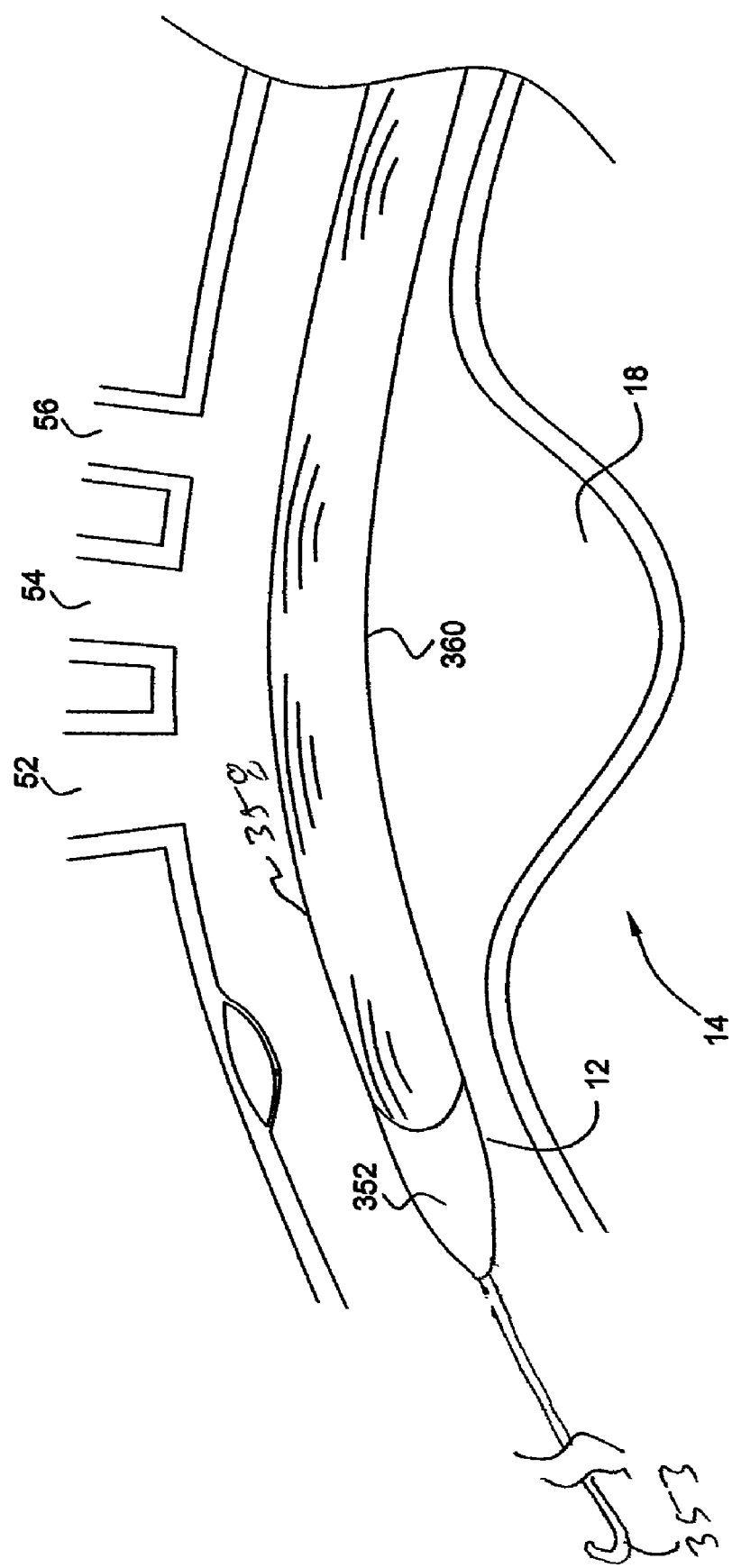
FIG. 13 is a view of the aortic arch of FIG. 12, showing a catheter in a position to deploy the stent graft therein.
Figure 14:
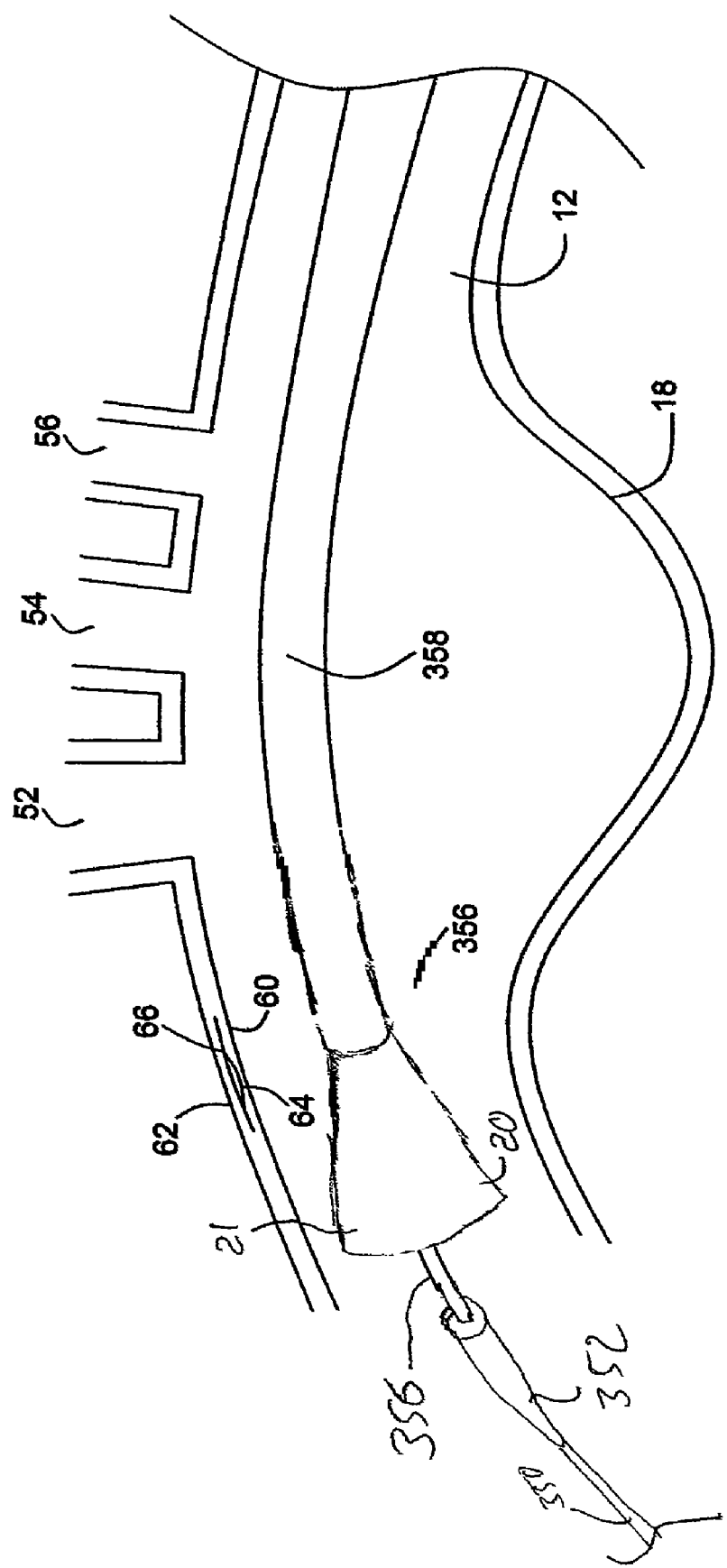
FIG. 14 is a view of the aortic arch as in FIG. 13, showing the stent graft partially deployed therein.

Referring now to FIGS. 9 through 14, a paradigm for deployment of the stent graft, in this example stent graft 20, into the aneurysmal aortic arch is shown. To prepare the stent graft 20 for delivery, the stent graft 20 in one loading process is first cooled with air cooled by vapors of liquid nitrogen and positioned over a delivery catheter as shown in FIG. 9, and then radially compressed, along its longitudinal axis 330 to the condition shown in FIG. 10, such that it has an outer diameter or cross section capable of being fitted into the crossing profile of a delivery sheath or catheter. (In another configuration a camera iris type compression cylinder can surround the device and press it uniformly to a small diameter—without cooling). Prior to compressing of the stent graft 20, a guidewire sheath central or middle member or catheter 356 is inserted through the inner circumference thereof, such that upon being compressed, the stent graft 20 surrounds and incorporates the middle member 356 extending therethrough. The stent graft 20, in its still cold state shown in FIG. 10 and having the middle member 356 disposed therethrough, is then held stationary as the outer sheath 358 of a catheter such as catheter 360 shown in FIG. 11 is moved into place surrounding the stent graft. A tapered tip 352 is disposed at the end of the middle member 356, such that the guidewire 350 (FIG. 13) may pass through the middle member 356 and through an open end of the tapered tip 352, and the tapered tip 352 also moves, with longitudinal movement of the middle member 356 with respect to the catheter outer sheath 358 (FIG. 14). The tapered tip 352 helps reduce the vessel trauma associated with guiding the catheter to the aneurysmal aorta location and, being of a tapered configuration, is more easily guided into and through restricted or smaller diameter regions of the lumen leading to the aneurysmal location than would be a catheter having a continuous diameter of the outer sheath 358. The middle member 356 also includes, a separate stop 370 (in cutaway of outer sheath 358 in FIG. 11) is fixedly positioned longitudinally on the middle member 356 with, respect to the outer sheath 358, such that, to deploy the stent graft 20, the outer sheath 358 is retracted while the stop 370 remains stationary. Thus, the stent graft remains stationary within the aortic arch while the retraction of the outer sheath 358 releases the stent graft 20 therefrom. The stent graft 20 is thus ready for deployment in an aneurysmal aortic arch.

For delivery of the stent graft 20 to the aneurysmal location, an incision (not shown) is made, preferably in the patient's leg or groin and into the femoral artery therein, and a guide wire 350 is guided into the artery through the incision and pushed along the artery in the direction of the aortic arch. The guide wire 350 is initially inserted such that the end 353 thereof passes through the aneurysmal site 14 and past the aneurysmal sac 18 location in the aorta 12 as shown in FIG. 12. To enable proper placement of the guide wire 350, the end 353 thereof may include a radiological marker thereon making the end 353 more easily visible through the use of a fluoroscope, although the guidewire 350 itself may be sufficiently fluoroscopically visible so as not to require the use of a marker. Likewise, the aorta 12 is radiologically marked, such as by injection of a liquid based radiological marker into the aorta 12 as part of the preparation of the patient for the placement of the stent graft 20, such that the aneurysmal sac 18 and the location of the branch arteries 52, 54, and 56 is readily visualized, with respect to the stent graft 20 and catheter, by the surgeon or other person deploying the stent graft 20. Thus, by viewing a fluoroscope which is directed to the aorta 12, the surgeon can properly locate the guide wire 350 and position the end 353 thereof adjacent to, and beyond, the aneurysmal sac 18. The guide wire 350 is used to guide the catheter 360, which has a substantially larger cross section than the guidewire 350, to the aneurysmal location 14 in the aorta 12.

Once the guide wire 350 is located as shown in FIG. 13, a catheter 360, having the compressed stent graft 20 located in a sheath 358 therein as described with respect to FIG. 11, is guided through the artery on the guide wire 350 to a position just upstream, of i.e., to the heart side, of the aneurysmal sac 18 as shown in FIG. 14. At this point in time, the stent graft 20 may be deployed. Prior to deployment, the tapered tip 352, on the end of guidewire sheath 356, may be slightly moved away from the outer sheath 358 as shown in FIG. 14, in the direction of the heart, by pushing on the middle member 356 thereby exposing the stent graft 20 through the open end of the outer sheath 358. To deploy the stent graft 20, the outer sheath 358 is then pulled back i.e., away from the heart and to the right in FIG. 14, while holding the middle member 356 and the stop 370 (FIG. 11) stationary. Thus the stent graft 20 is maintained in a stationary position in the aorta 12 resulting in the stent graft 20 being left behind in the aorta 12, the first hoop 21 thereof seen emerging from the outer sheath 358 in FIG. 14. Because the stent graft according to the present embodiment is constructed of a shape memory material, the stent graft 20 will expand towards its as made state (relaxed—low energy), i.e., as shown in FIG. 4B, without the need for an inflation device. During deployment, the stent graft 20 must be positioned such that its opposed ends span the aneurysmal sac 18, and the window 32 thereof must be positioned to span the three branch arteries 52, 54, and 56. To accomplish this, the stent graft 20 may include radiological markers thereon (not shown), the orientation and position of which, relative to the branch arteries 52, 54 and 56 and the aneurysmal sac 18, are used by the surgeon to properly deploy the stent graft 20. Once the stent graft 20 is rotationally and longitudinally properly positioned in the aorta 12, the outer sheath 358 is fully retracted to release the stent graft 20 into the deployed position as shown in FIG. 7, and the catheter 360 composed of the guide wire 350, tapered tip 352, middle member 356 and outer sheath 358 are removed through the leg incision.

Figure 15:
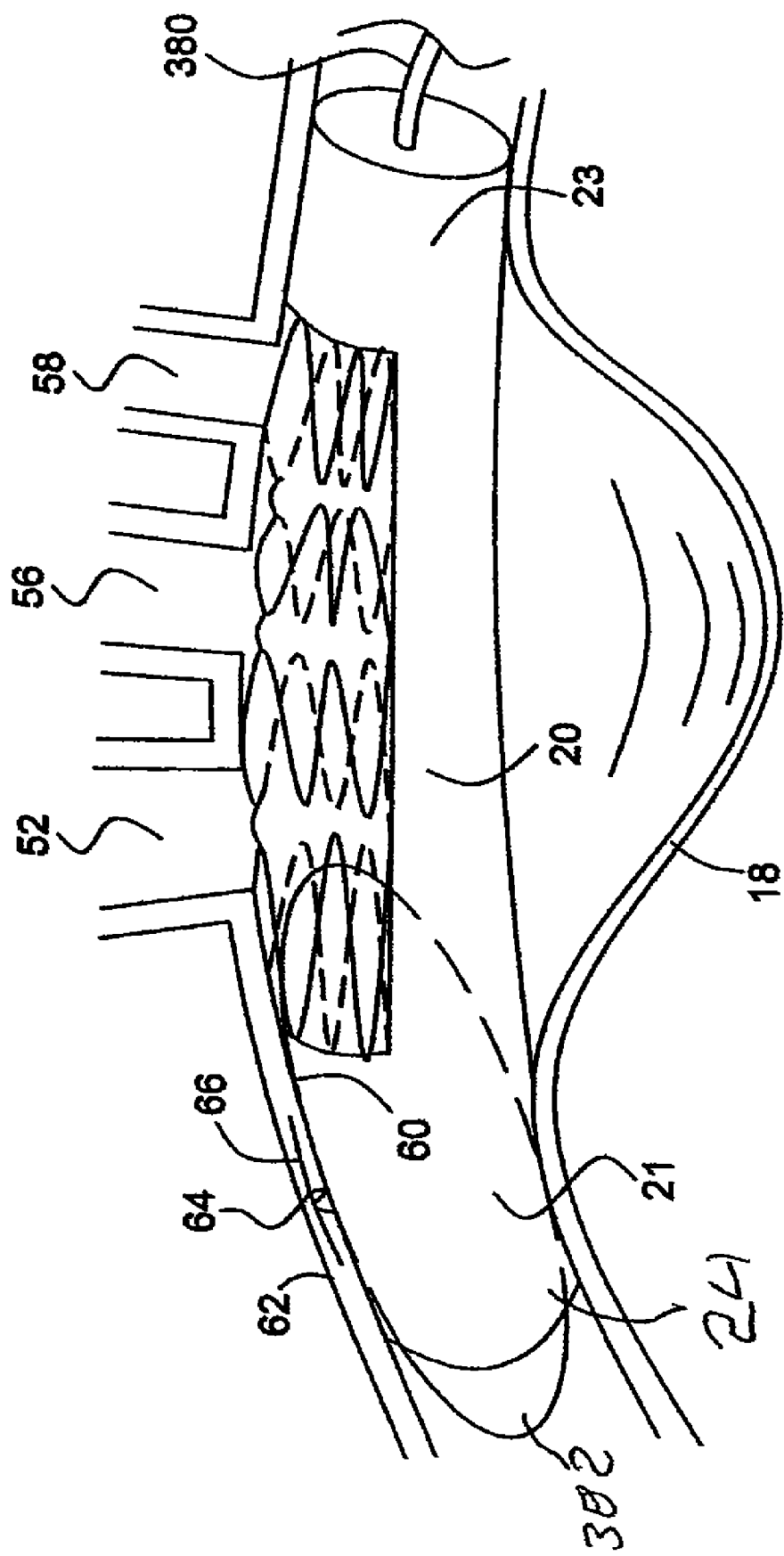
FIG. 15 is a view of the aortic arch of FIG. 7, showing the stent graft of FIG. 4B deployed therein and a balloon catheter deployed within the stent graft to additionally configure portions thereof in the aorta.

After the stent graft 20 is deployed, the surgeon may utilize a balloon catheter 380, as shown in FIG. 15, into the interior of the deployed stent graft 20, and use a contrast saline solution mix to inflate a balloon 382 contained therein and extendable therefrom, to slightly expand or assure full expansion of the stent graft 20, and to remove any wrinkles in the graft material 24. During this procedure, the balloon should only be inflated within the bounds of the first and second hoops 21, 23, so as not to over-extend the stents 22b-22e into the aorta wall. Once this procedure is completed, the balloon 382 may be deflated, the catheter 380 removed, and the incisions in the artery and leg or groin closed. Each of the embodiments of the stent graft shown and described herein are likewise deployable using this technique, such that the windows therein are alignable with the branch arteries 52, 54, and 56 to prevent the blockage of the branch arteries intersection with aorta 12.

The stent grafts of the embodiments shown and described herein have been described in terms of using a shape memory material as the stent material. Alternatively, other biocompatible materials such as stainless steel could be used to form the stent portions of the stent graft. In such a case, the deployment of the stent graft into the aorta might require the use of an inflation device, positioned within the stent graft, which could be inflated to cause the stent graft to retake it's as-manufactured (relaxed/unconstrained) form. Such an inflation device can be a balloon, which is located in, and spans the length of, the stent graft within the circumference prescribed by the graft portion, and is attached to a tube extending outwardly therefrom. When the stent graft is compressed and configured for placement in a catheter, the balloon is located therein, and the tube is fed down the catheter such that the surgeon can apply a pressure source to the tube to direct a contrast liquid or other fluid, under pressure, to the balloon, to inflate the stent graft at the appropriate time. Upon completion of the deployment of the stent graft, the balloon is removed with the catheter.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material, or process to the objective, spirit and scope of the present invention. All such modifications are intended to be within the scope of the invention.

All references cited herein are to aid in the understanding of the invention, and are incorporated in their entireties for all purposes.

What is claimed is:

1. A stent graft for spanning, and sealing off, an aneurysmal location in the aortic arch adjacent to the branch arteries extending from the aortic arch, comprising:
   a tubular graft material having a first end hoop and a second end hoop formed as segments of said tubular graft material at first and second ends of the tubular graft material, said first and second hoops separated by a window portion and a corresponding spanning portion of graft material, said window portion and corresponding spanning portion providing a circumferential perimeter;
   a first intermediate hoop and a second intermediate hoop of graft material dividing said window portion into first, second and third window portions, each of said first, second and third window portions being sized and positioned to span the intersection of one of the branch arteries in the aortic arch;
   a first stent engaged with, and outwardly biasing, said first end hoop;
   a second stent received within, and outwardly biasing, said second end hoop; and
   a third stent having a plurality of staggered, opposed first and second apexes separated by struts, said third stent disposed in a spanning relation of said first window, said first set of apexes of said third stent extending within and restrained by the first end hoop and the second set of apexes of the third stent extending within and restrained by said first intermediate hoop;
   a fourth stent having a plurality of staggered, opposed first and second apexes separated by struts, said fourth stent disposed in a spanning relation of said second window, said first set of apexes of said third stent extending within and restrained by the first intermediate hoop and the second set of apexes of the fourth stent extending within and restrained by said second intermediate hoop; and
   a fifth stent having a plurality of staggered, opposed first and second apexes separated by struts, said fifth stent disposed in a spanning relation of said third window, said first set of apexes of said fifth stent extending within and restrained by the second intermediate hoop and the second set of apexes of the fifth stent extending within and restrained by said second end hoop.

* * * * *